United States Patent [19]

Kitagawa

[11] Patent Number: 4,693,968
[45] Date of Patent: Sep. 15, 1987

[54] AGENT FOR QUANTITATIVE DETERMINATION OF MICROORGANISMS

[75] Inventor: Tsunehiro Kitagawa, Nagasaki, Japan

[73] Assignee: Dainippon Pharmaceutical Co., Ltd., Japan

[21] Appl. No.: 643,281

[22] Filed: Aug. 22, 1984

[30] Foreign Application Priority Data

Aug. 24, 1983 [JP] Japan .................................. 58-155602

[51] Int. Cl.$^4$ ................. G01N 53/00; G01N 33/541; C12Q 1/02; C12Q 1/04
[52] U.S. Cl. ........................................... 435/7; 435/29; 435/34; 435/810; 436/540
[58] Field of Search ................... 435/4, 7, 810, 29, 34; 436/518, 519, 540, 824

[56] References Cited

PUBLICATIONS

S. K. Sarafian et al., "Detection of Gonococcal Antigens by an Indirect Sandwich Enzyme Linked Immunosorbent Assay," *J. Med. Micro.* 15: 541–550, (1982).

D. C. Dodd et al., "Antigenic Quantitation of Type 1 Fimbriae on the Surface of *Escherichia coli* Cells by an Enzyme-Linked Immunosorbent Inhibition Assay," *Infect. Immun.* 38(2): 764–773, (1982).

Primary Examiner—Sidney Marantz
Assistant Examiner—Shawn P. Foley
Attorney, Agent, or Firm—Scully, Scott, Murphy & Presser

[57] ABSTRACT

An agent for quantitative determination of microorganisms, which comprises (a) an antibody prepared from a strain of the same species as the species of microorganisms to be determined, (b) an insolubilized cell component of a strain which can sufficiently bind to the antibody (a) but does not release and replace to other strains which have been bound with the antibody (a), and (c) a labelled second antibody, and a method for the quantitative determination of microorganisms. The agent and method of the present invention are useful for determinating simultaneously not only a strain from which the antibody is prepared but also other strains of the same species which are contained in the test sample.

3 Claims, 3 Drawing Figures

AGENT FOR QUANTITATIVE DETERMINATION OF MICROORGANISMS

The present invention relates to an agent for quantitative determination of microorganisms. More particularly, it relates to an agent for quantitative determination of microorganisms comprising the following components:

(a) an antibody prepared from a strain of the same species as the species of microorganisms to be determined, (b) an insolubilized cell component of a strain which can sufficiently bind to the antibody (a) but does not release and replace to other strains which have been bound with the antibody (a), and (c) a labelled second antibody.

Various microorganisms such as bacteria, actinomycetes, fungi cause rot of foods and various diseases in animals and plants, and hence, it is very important to determine quantity of the microorganisms in order to know the degree of rot or degree of infection. There have hitherto been known various methods for the quantitative determination of microorganisms, for example, (i) a method of counting the number of colonies of microorgnisms by naked eyes, and (ii) a method of determining impedance, change of pH value, or amount of consumed oxygen, produced carbon dioxide, metabolites, or produced enzymes, which are induced by the presence of microorganisms. However, these methods (i) and (ii) must be applied to the test samples after pre-treatment for inhibiting growth of other microorganisms, and hence, they require much time for preparation thereof. Besides, the method must be done after culturing for 24 hours in order to grow the microorganism to be determined, becuase, otherwise, the sensitivity is very low. Thus, these methods can not be applied to rapidly.

It is recently tried to determine the microorganisms by utilizing antigen-antibody reaction. For example, Sarafian et al. have tried to determine an antigen common to all strains of genococci by sandwiching whole cells, lipopolysaccharides or outer membrane proteins of the genococcus with an anti-genococcus whole cell rabbit antibody and an insolubilized anti-genococcus whole cell mouse antibody, followed by adding an enzyme-labelled anti-rabbit IgG goat antiserum [cf. J. Med. Microbiol., 15, 541–550 (1982)]. The outer membrane proteins are an antigen common to all strains, and the outer membrane proteins obtained from each strain are determined in a single system in the above method. However, in order to apply this method to the quantitative determination of microorganisms, the microorganisms must be cultured in order to extract the outer membrane proteins therefrom, which is troublesome, and further, such a common antigen is not necessarily present in all microorganisms other than genococci. Besides, Dodd et al. have tried to determine *Escherichia coli* by competing the test sample microorganism with insolubilized flagella of *E. coli* against an antibody prepared from the falgella of *E. coli*, followed by adding thereto an enzyme-labelled second antibody [cf. Infect. Immun., 38, 764–773 (1982)]. According to this method, the collected test samples can be used as they stand with high sensitivity. Althouth the strain used for the preparation of an antibody can be determined with very high sensitivity by this method, other strains can almost not be determined. For example, in case of determining *E. coli* contained in foods, it is impossible to determine total number of all of *E. coli* strains contained in the foods.

Thus, according to the conventional methods for the quantitative determination of microorganisms, only a specified strain can be determined among the microorganisms contained in the test sample, but total or some groups of strains of microorganisms can not simultaneously be determined.

The present inventor has studied on an improved method for the quantitative determination of microorganisms without the drawbacks in the known methods, and has thought that the reason why the known methods can determine merely a specific strain is that the strain to be used for the preparation of an antibody for insolubilization (or the strain for insolubilizing) is the same as the strain to be used for the preparation of the antibody. Then, the present inventor has used an insolubilized strain which can sufficiently bind with the antibody but the binding is weak and has tired to apply said strain to the test sample in the conventional competition method. As a result, it has been found that the insolubilized strain has a low affinity to the antibody and the amount of antibody bound to the insolubilized strain is very low, and hence, such a method can not practically be used.

As a result of a further study, it has now been found that the desired quantitative determination of microorganisms can be done by subjecting an excess amount of an antibody prepared from a strain of the same species as the species of the microorganisms to be determined to an antigen-antibody reaction with the microorganisms contained in the test sample, and then counting the remaining antibody which has not reacted with the microorganisms in the test sample. That is, it has been found that when an insolubilized cell component of a strain which can sufficiently bind to the free antibody but does not release and replace to other strains which have been bound with the antibody is used and the remaining antibody which has not reacted with the microorganisms in the test sample is bound with the insolubilized strain, the antibody bound with the insolubilized cell component is easily quantitatively determined, from which the quantity of the antibody bound to the strains in the test sample (in turn the quantity of the strains in the test sample) can be calculated backward.

An object of the present invention is to provide an improved agent for the quantitative determination of microorganisms, which can be useful for simultaneous determination of a group of strains of the same species in the microorganisms contained in the test sample. Another object of the invention is to provide a method for the quantitative determination of a group of strains of species in the microorganisms contained in test samples. These and other objects and advantages of the present invention will be apparant to those skilled in the art from the following description.

The agent for quantitative determination of microorganisms of the present invention comprises the following components:

(a) an antibody prepared from a strain of the same species as the species of microorganisms to be determined, (b) an insolubilized cell component of a strain which can sufficiently bind to the antibody (a) but does not release and replace to other strains which have been found with the antibody (a), and (c) a labelled second antibody.

According to the present invention, the determination is carried out by steps of (i) adding an excess and predetermined amount of the antibody (a) to the test sample in order to subject them to an antigen-antibody reaction, (ii) adding the insolubilized cell component (b) to the reaction mixture in order to react the remaining antibody which has not reacted with the antigen (microorganisms) contained in the test sample, (iii) separating the precipitated antibody (a) - antigen (b) complex, (iv) adding thereto the labelled second antibody (c), (v) washing the mixture with phosphate buffer, and then measuring the activity of labelled substance in the complex. According to the above method, the amount of the antibody in the solid phase is determined, and hence, the amount of the antibody in the liquid phase is calculated, based on which the amount of microorganisms contained in the test sample can be quantitatively determined.

The agent of the present invention is usually in the form of a kit, and may optionally be used in a combination with a standard solution containing a predetermined amount of microorganism useful for preparing a calibration curve, an agent for determining the activity of the labelled substance (e.g., in case of enzyme-labelled antibody, the agent comprises a substrate, a substrate-diluent, an enzyme-reaction terminater, etc.), and a buffer, in addition to the above components (a) to (c).

The antibody (a) is usually prepared by disrupting the culture cells of a strain microorganisms to separate the cell components (e.g. cell walls, etc.), mixing the separated components with an appropriate adjuvant, administering subcutaneously or intramuscularly the mixture to animals such as rabbit, guinea pig, goat, sheep, etc., collecting a blood serum from the animals, and treating the collected serum in a usual manner. The strain may be any strain among the same species of the microorganisms which are contained in the test sample.

The insolubilized cell component (b) can be prepared by culturing a strain which can sufficiently bind to the antibody (a) but does not release the binding of the antibody (a) with other strains (antigen) contained in the test sample, disrupting the culture cells to separate the cell components (e.g. cell walls, etc.), and binding the separated cell components to an insoluble carrier, such as natural insoluble polysaccharides, chemically treated dextran gels, agar gels, plastic beads, acrylamide gels, glass beads, metal oxide powders, synthetic rubber tube, or the like. When the cells per se are insolubilized, they may disadvantageously bind with other microorganisms. For the binding, various binding agents are used depending on the insoluble carriers, for example, glutalaldehyde, toluenediisocyanate, dihalogeno-nitrobenzene, etc. for chemically binding the amino group in the cell walls with the amino group in the insoluble carrier, and maleimide derivatives [e.g. N-(γ-maleimidobutyloxy)succinimide, etc.] or the like for binding the amino group in the cell walls with the thiol group in the insoluble carrier.

The labelled second antibody (c) can be prepared by labelling an antibody (second antibody) against γ-globulin (IgG) of the animal which is used for the preparation of the antibody (a). The labelling is carried out by using enzymes, radioisotopes, fluorescent compounds, spin compounds, etc. In case of an enzyme-labelled second antibody, it is easily prepared by binding an enzyme with the second antibody in the same manner as in the binding between the cell walls and the insoluble carrier as mentioned above. Suitable examples of the enzyme are β-galactosidase, peroxidase, lipase, alkaliphosphatase, glucose-6-phosphate dehydrogenase, etc.

The agent of the present invention is advantageous in that the test sample can be immediately applied to without culturing and can be useful for comprehensively determining a group of strains of species in the microorganisms contained in the test sample, and is particularly useful for the quantitative determination of bacteria (e.g. *Escherichia coli*, *Streptococcus mutans*), actinomycetes (e.g. *Streptomyces scabies*), fungi (e.g. *Pyricularia oryzae*), or the like.

Figure 1:
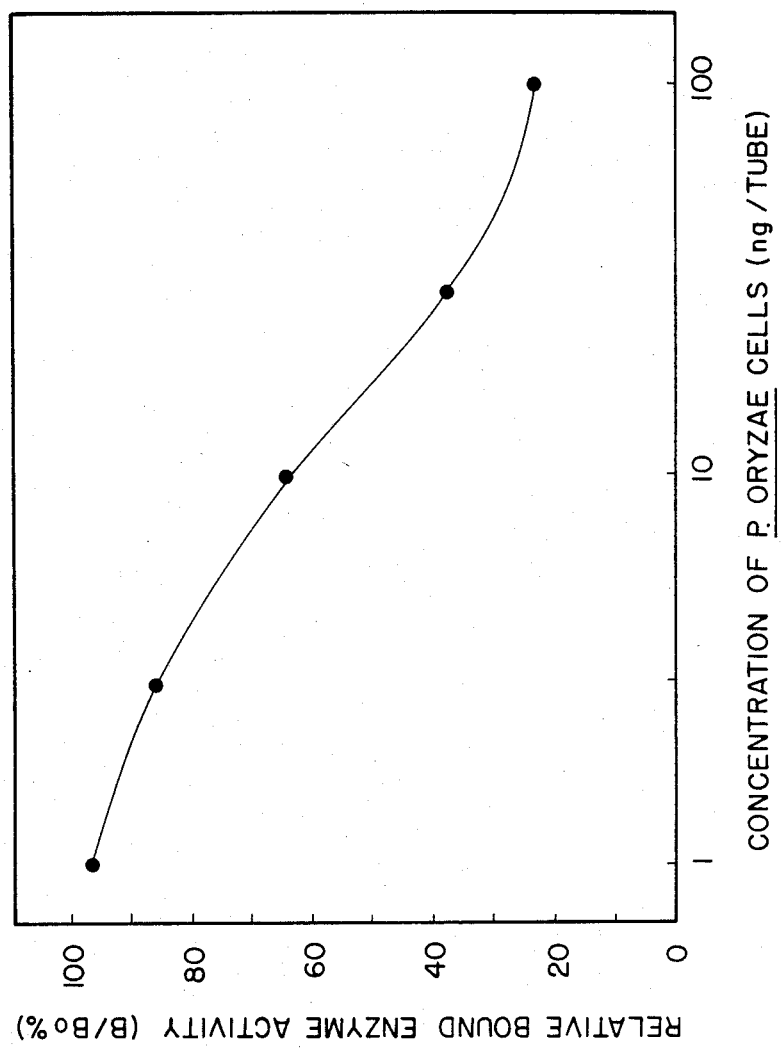
FIG. 1 demonstrates the results of quantitative detection of the presence of *Pyricularia oryzae* in a test sample utilizing the method of the present invention.

The present invention is illustrated by the following Examples but should not be construed to be limited thereto.

EXAMPLE 1

Preparation of antiserum of *Streptomyces scabies* Obama strain (i) Preparation of cell walls:

*Streptomyces scabies* Obama strain is inoculated in a medium (200 ml) containing $K_2HPO_4$ (0.1 g), asparagin (0.1g), glucose (2 g) and 15% extract of potato (40 ml), and the mixture is cultured with shaking for 7 days. The cells are collected by filtration, washed with purified water twice and then lyophilized to give dried cells (1 g). The dried cells thus obtained are suspended in a 0.02M phosphate buffer containing 0.9% sodium chloride (100 ml), and the mixture is treated with a ultrasonic disintegrator (Bransons sonifier W 185 type, 60 W) for 15 minutes under ice-cooling. The resulting mixture is centrifuged at 2,200 rpm for 10 minutes, and precipitates are collected, washed twice with purified water (5 ml) and then lyophilized to give the desired cell walls (0.1 g), which is kept at 4° C. ps (ii) Immunization Cell walls (0.5 mg) obtained above are suspended in 0.9% NaCl (0.5 ml) and thereto is added an incomplete Freund's adjuvant (0.5 ml) to emulsify the mixture. The emulsion is subcutaneously or intramuscularly injected to rabbit. The injection is repeated 4 times at two weeks intervals, and ten days after the final injection, the rabbit is bled.

EXAMPLE 2

Preparation of antiserum of *E. coli* K 12 strain (i) Prepartion of cell walls:

*E. coli* K 12 strain is inoculated in a bouillion medium (manufactured by Difco Laboratories, U.S.A., 2,000 ml) and the mixture is cultured with shaking overnight. The cells are collected by centrifuging at $20,000 \times g$ for 30 minutes, washed twice with 0.02M phosphate buffer containing 0.15M sodium chloride and then lyophilized to give dried cells (2 g). The dried cells thus obtained are suspended in a 0.02M sodium chloride-containing phosphate buffer (100 ml), and the mixture is treated with a ultrasonic disintegrator (the same as used in Example 1) for 10 minutes under ice-cooling. The resulting mixture is centrifuged at $20,000 \times g$ for 30 minutes, and the precipitates are collected, washed twice with purified water (20 ml) and then lyophilized to give the desired cell walls (0.1 g), which is kept at 4° C.

(ii) Immunization

The cell walls obtained above are treated in the same manner as described in Example 1 (ii) to give the desired antiserum.

EXAMPLE 3

Preparation of antiserum of *Pyricularia oryzae* 001 Kyu 82-05A strain (i) Preparation of cell walls:

In the same manner as described in Example 1 (i) except that *Pyricularia oryzae* 001 Kyu 82-05A strain is used and a medium containing $KH_2PO_4$ (0.1 g), $K_2HPO_4$ (0.1 g), $MgSO_4$ (0.1 g), $CaCl_2$ (0.02 g), glucose (4 g) and yeast extract (1 g) is used as the medium, there are obtained the desired cell walls. ps (ii) Immunization The cell walls obtained above are treated in the same manner as described in Example 1 (ii) to give the desired antiserum.

EXAMPLE 4

Prepartion of antiserum of *Streptococcus mutans* No. 6715 strain (i) Prepartion of cell walls:

*S. mutans* No. 6715 strain is inoculated in a brain heart infusion medium (manufactured by BBL Co., 1,000 ml) and cultured. The cells are collected by centrifuging at $10,000 \times g$ for 15 minutes, washed twice with distilled water, and lyophilized to give dried cells (0.6 g). The dried cells thus obtained are suspended in 0.02M phosphate buffer containing 0.15M sodium chloride (100 ml) and the mixture is treated with a ultrasonic disintegrator (the same as used in Example 1) for 15 minutes under ice-cooling. The resulting precipitates are collected by centrifuging at $20,00 \times g$ for 30 minutes, washed twice with purified water (20 ml) and then are again treated with a ultrasonic disintegrator under the same condition as above for 45 minutes. The resulting mixture is lyophilized to give the desired cell walls (0.1 g), which is kept at 4° C.

(ii) Immunization

The cell walls contained above (0.5 mg) are suspended in a 0.9% NaCl (0.5 ml) and thereto is added an incomplete Freund's adjuvant (0.5 ml) to emulsify the mixture. The emulsion is intravenously injected to rabbit. The injection is repeated 3 times at two weeks intervals, and just before each injection, the rabbit is bled. The collected blood is kept at $-30°$ C.

EXAMPLE 5

Preparation of an insolubilized antigen

An Amino-Dylark cylinder (manufactured by Sekisui Kagaku K.K., hereinafter referred to as "AD") which is washed with a detergent, SCAT-20X (manufactured by Daiichi Kogyo Seiyaku, K.K.) is immersed in a 1% glutaraldehyde for 1 hour and then washed with 0.01M phosphate buffer (pH 7.0) containing 0.9% sodium chloride. The aldehyde-introduced AD thus obtained (100 cylinders) are immersed in a suspension of cell walls (100 μg) of *Streptomyces scabies* Aino strain, *E. coli* No. 45 strain, *Pyricularia oryzae* 031 Ine 72 strain or *Streptococcus mutans* HS-6 strain [which is prepared in the same manner as described in Example 1 to 4, (i)] in 0.02M phosphate buffer containing 0.9% sodium chloride (10 ml), and the mixture is shaken at room temperature for 0.5 hour and at 4° C. for 2 hours. The reaction mixture is washed with a 0.01M EDTA - 0.1% BSA-containing 0.06M phosphate buffer (pH 7.4) (hereinafter, referred to as "Buffer A") to give the desired insolubilized antigen, which is kept in Buffer A at 4° C.

EXAMPLE 6

Preparation of an enzyme-labelled second antibody

To an anti-rabbit IgG goat serum (manufactured by Miles corporation, U.S.A., 5 ml) is added a 0.1M phosphate buffer (pH 7.0, 5 ml), and to the mixture is added an aqueous saturated ammonium sulfate (10 ml) under ice-cooling, and the mixture is stirred for 20 minutes and then centrifuged at $12,000 \times g$ for 10 minutes to collect the precipitates. The above procedure is repeated twice. The precipitates thus obtained are dissolved in a 0.1M phosphate buffer (pH 7.5, 5 ml). The solution is dialyzed against a 0.9% NaCl-0.02M phosphate buffer (pH 7.0) (2,000 ml) at ° C. for 24 hours to give an anti-rabbit IgG goat serum IgG fraction. The fraction (6 ml) thus obtained is dissolved in a 0.1M phosphate buffer (pH 6.0) (1 ml), and the solution is mixed with a solution (0.5 ml) of N-(γ-maleimidobutyloxy)succinimide (1 mg/ml) in tetrahydrofuran. The mixture is stirred at room temperature for 30 minutes. The reaction mixture (50 μl) is added to a solution of β-galactosidase (500 μg) in a 0.1M phosphate buffer (pH 6.0) (1 ml), and the mixture is stirred for 30 minutes. The reaction mixture is passed through a column of Sepharose 6B (manufactured by Pharmacia, Sweden) (2 cmφ×38 cm) which is equilibrated with a 0.1M NaCl - 1 mM $MgCl_2$-0.1% BSA-0.1% $NaN_3$ containing 0.02M phosphate buffer (pH 7.0) (hereinafter, referred to as "Buffer B"), and then eluted with Buffer B, wherein each fraction contains 3 ml of eluate. The enzymatic activity of each fraction is measured by the method of Aikawa, T. et al [cf. Endocrinology, 105, 1-6 (1979)], and a fraction having a peak enzymatic activity is collected to give the desired β-galoctodiose-labelled second antibody.

EXAMPLE 7

Qantitative determination of a test sample containing microorganisms

To a test sample containing *Pyricularia orzyae* (100 μl) is added a 20,000 folds diluted solution (100μl) of the antiserum prepared in Example 3 in a test tube, and the mixture is reacted at room temperature overnight. To the reaction mixture is added the insolubilized antigen prepared in Example 5 in an excess amount, and the mixture is shaken at 25° C. for one hour. The reaction mixture is washed twice with Buffer B (1 ml), and thereto is added the β-galactosidase-labelled second antibody (0.2 ml) prepared in Example 6 (the β-galactosidase activity: 200 μU; 1 U means an amount necessary for hydrolyzing 1 μmol of the substrate for 1 minute), and the mixture is shaken at 30° C. for 4 hours. The mixture is washed twice with Buffer B (1 ml), and thereto is added 0.1 nM 7-β-D-galactopyranosyloxy-4-methylcoumarine (150 μl), and the mixture is incubated at 30° C. for 30 minutes. To the reaction mixture is added a 0.2M glycine-NaOH buffer (pH 10.3, a reaction terminater) (2.5 ml) to terminate the enzyme reaction. The fluorescent intensity of 7-hydroxy-4-methylcoumarine produced by the enzyme reaction is measured spectrofluormetrically.

A standard curve is drawn on a semilogarithmic coordinate paper, as shown in the accompanying FIG. 1, wherein the ordinate axis is relative bound enzyme activity (B/Bo%) and the abscissa axis is a concentration of *Pyricularia oryzae* (ng/tube). According to this method, 1 ng to 100 ng of *Pyricularia oryzae* can be measured per one test tube.

In the same manner as described above, the content of *E. coli*, *Streptomyces scabies* and *Streptococcus mutans* can be measured.

EXAMPLE 8

Comparison of cross reactivity due to the difference of the strains of microorganisms used for solid phase In the same manner as described in Example 7 except than an antibody from *Pyricularia oryzae* 001 Kyu 82-05A strain and an insolubilized product of said strain were used, the quantitative determination of the strain was done. As a result, only the same strain as used above was determined.

Among various stains of *Pyricularia oryzae* as shown in the following Table 1, 037 Ken 60-19 strain was elected, and an insolubilized product of said strain was used as the standard strain and subjected to the determination likewise. As a result, it showed a cross reactivity with other strains as shown in Table 1. Besides, when an insolubilized strain of 031 Ine 72 strain which showed the weakest cross reactivity among the test strains was used and subjected to comparison of the cross reactivity, likewise. The result is shown in Table 2.

TABLE 1

| Strain | Cross reactivity (%) |
| --- | --- |
| 001 Kyu 82-05A | 121.7 |
| 003 Ken 54-20 | 21.8 |
| 007 Kita 1 | 34.6 |
| 031 Ine 72 | 9.2 |
| 037 Ken 60-19 | 100.0 |
| 047 F67-57 | 46.9 |
| 101 Ine 168 | 74.2 |
| 102S Kyu 77-07A | 52.3 |
| 137 Ken 53-33 | 14.8 |
| 103S Kyu 79-160A | 88.5 |

TABLE 2

| Strain | Cross reactivity (%) |
| --- | --- |
| 001 Kyu 82-05A | 100.0 |
| 003 Ken 54-20 | 41.3 |
| 007 Kita 1 | 23.0 |
| 031 Ine 72 | 41.3 |
| 037 Ken 60-19 | 233.1 |
| 047 F67-57 | 380.0 |
| 101 Ine 168 | 339.3 |
| 102S Kyu 77-07A | 100.0 |
| 137 Ken 53-33 | 126.7 |
| 103S Kyu 79-160A | 324.8 |
| *E. coli* K 12 | <0.0001 |
| *Streptomyces scabies* Obama | 0.04 |
| *Streptomyces scabies* Higashihara | 0.03 |

As is clear from the comparison of the data of Table 1 and Table 2, the reactivity of all strains shown in Table 2 increased and all strains other than 001 Kyu 82-05A strain can be determined. Besides, it is clear from Table 2 that any strains of other species is not determined.

EXAMPLE 9

Comparison of cross reactivity due to the difference of the strains used for solid phase In the same manner as described in Example 7 except that an antibody prepared from *Streptococcus mutans* No. 6715 strain and an insolubilized product of said strain were used, the quantitative determination of the strain was done. As a result, the strain showed the cross reactivity as shown in the accompanying FIG. 2. The quantitative determination was done likewise by using an insolubilized product of HS-6 strain which showed the weakest cross reactivity among the strains in FIG. 2. The result is shown in FIG. 3.

Figure 2:
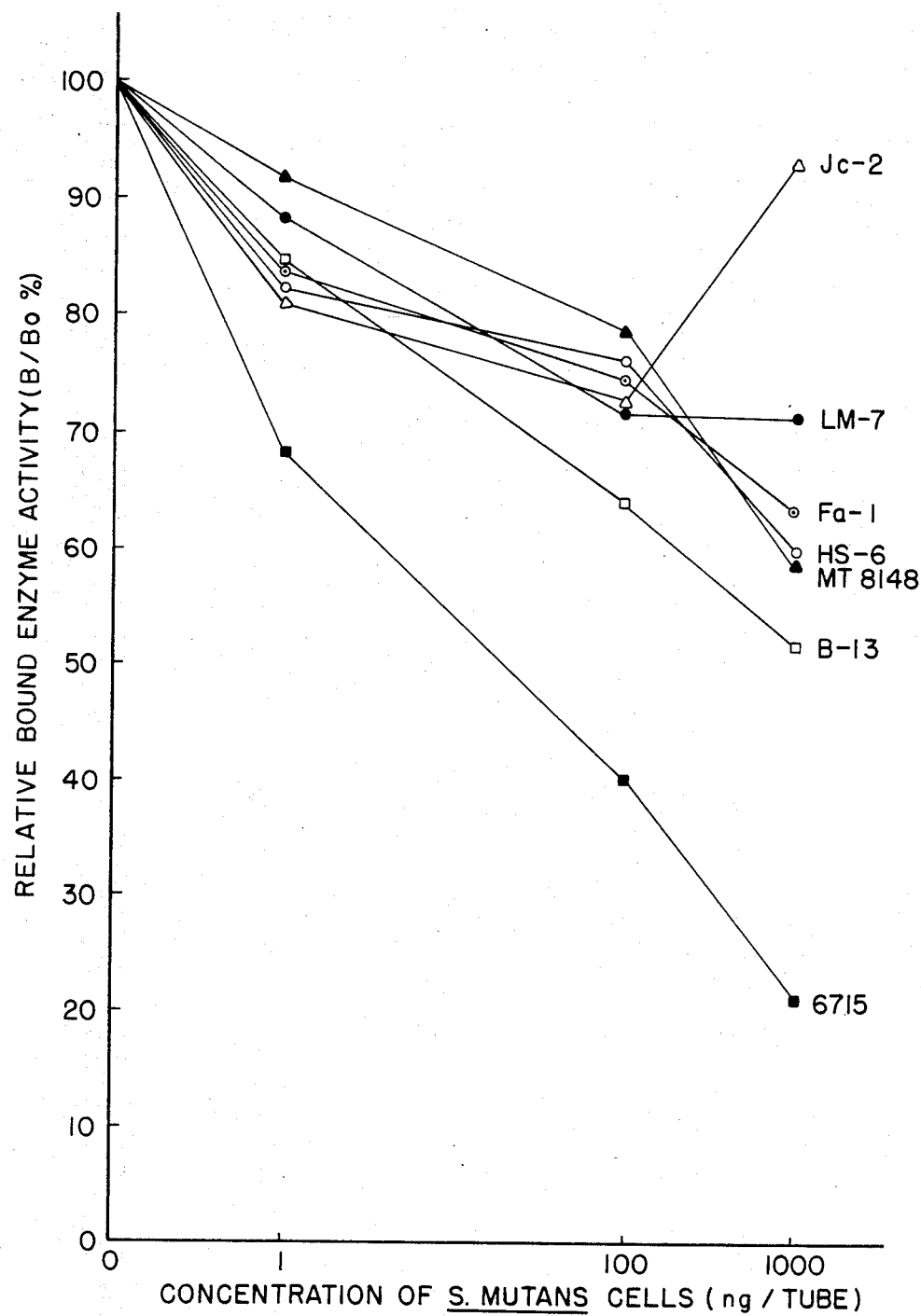
FIG. 2 presents a comparison of cross-reactivity of several strains of *Streptococcus mutans* when the antibody and the insolubilized cell walls are derived from the same strain.
Figure 3:
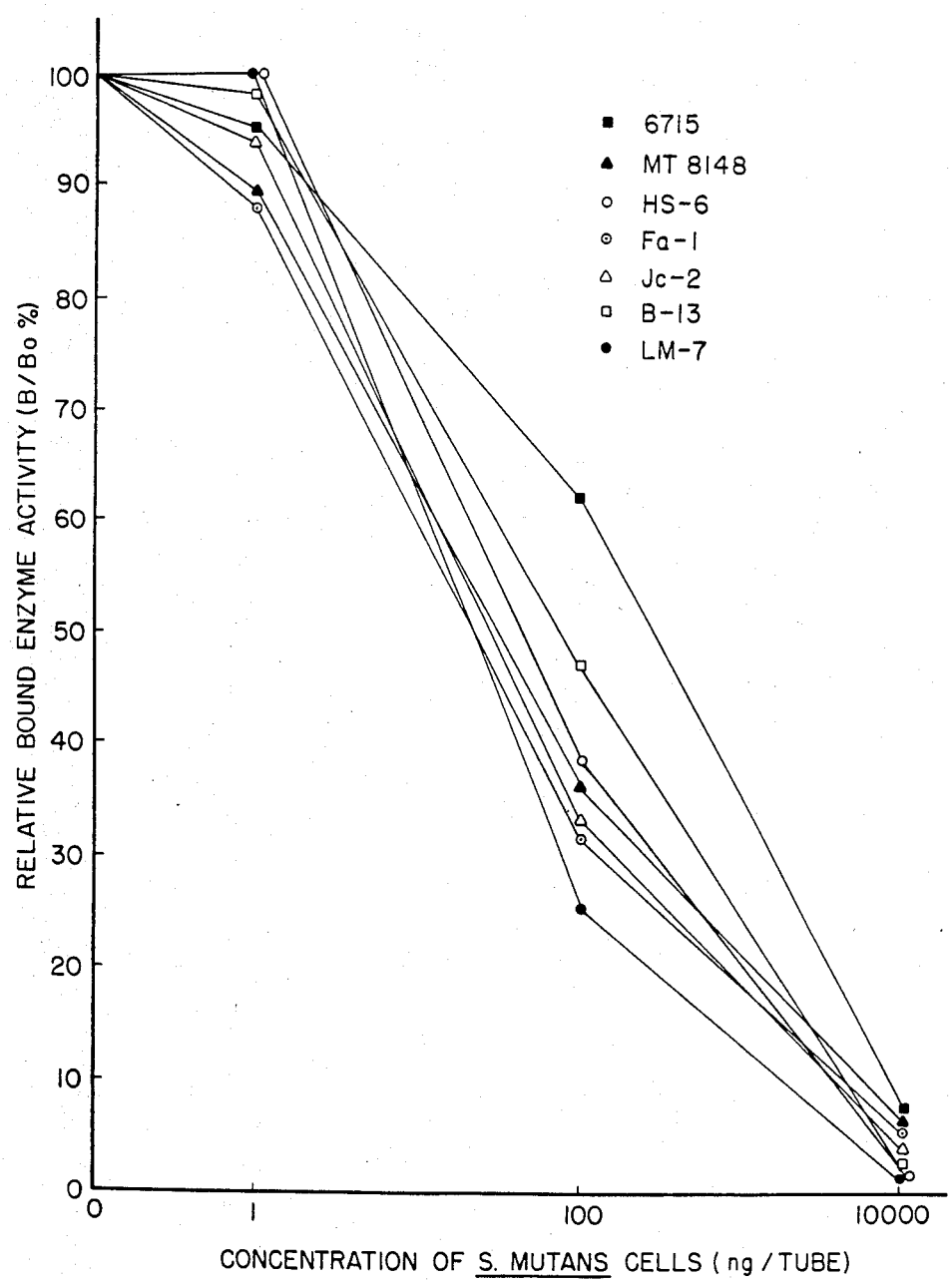
FIG. 3 demonstrates the results obtained with the use of the insolubilized cell walls of a strain of *S. mutans* which is only weakly cross-reactive with the antibody employed.

As is clear from the comparison of the data in FIG. 2 and FIG. 3, each strain in FIG. 3 showed increased reactivity, which means that strains other than No. 6715 strain can also be sufficiently determined.

EXAMPLE 10

Accuracy and precision of the value measured by the agent of the present invention A test sample containing strains of *Pyricularia oryzae* was repeatedly tested 5 times within a day (i.e. intra-assay) and further tested one time per day for 5 days (i.e. inter-assay), and the mean of the data and the standard deviation were calculated. The results are shown in Table 3.

TABLE 3

| | Added sample (ng/tube) | Measured* (ng/tube) | Recovery (%) | Coefficient of variation (%) | Number of assays |
| --- | --- | --- | --- | --- | --- |
| Intra-assay | 1 | 1.01 ± 0.05 | 101.0 | 5.0 | 5 |
| | 3 | 2.96 ± 0.12 | 98.7 | 4.1 | 5 |
| | 10 | 10.44 ± 0.74 | 104.4 | 7.1 | 5 |
| | 30 | 32.90 ± 3.44 | 109.7 | 10.5 | 5 |
| | 100 | 104.8 ± 5.40 | 104.8 | 5.2 | 5 |
| Inter-assay | 1 | 1.01 ± 0.15 | 101.0 | 14.9 | 5 |
| | 3 | 3.13 ± 0.23 | 104.3 | 7.3 | 5 |
| | 10 | 10.29 ± 0.54 | 102.9 | -5.2 | 5 |
| | 30 | 28.9 ± 1.97 | 96.2 | 6.8 | 5 |
| | 100 | 104.9 ± 7.44 | 104.9 | 7.1 | 5 |

*Mean ± S.D.

As is clear from Table 3, the agent of the present invention showed less difference in intra-assay and also in inter-assay, which means that the agent of the present invention can be used for the quantitative determination of microorganisms with high accuracy and percision.

What is claimed is:

1. A kit for quantitative determination of a group of strains belonging to a single species of microorganism, the determination being based on non-competitive antigen-antibody reaction, which comprises:
   (i) a first antibody raised against a first strain which belongs to the same species of the microorganism to be determined, the first antibody having affinity for more than one strain of the species,
   (ii) insolubilized cell walls of a second strain belonging to the same species of microorganism to be determined which differs from the first strain in having a lower affinity for the first antibody than the first strain, and
   (iii) a labelled second antibody, having affinity for the first antibody.

2. The kit according to claim 1, wherein the first antibody as component (i) is antiserum obtained by immunizing an animal with cell walls of the first strain, and the insolubilized cell walls as component (ii) are cell walls of the second strain which are insolubilized with an insoluble carrier.

3. A method for the quantitative determination of a group of strains belonging to same species of microorganism based on non-competitive antigen-antibody reaction, which comprises the following six steps:

step (i) adding a first antibody raised against a first strain which belongs to the species of the microorganism to be determined, the antibody having affinity for more than one strain of the species, to a test sample suspected of containing the microorganism to be determined, in order to subject them to non-competitive antigen-antibody reaction, wherein the amount of the first antibody added is predetermined and excessive as compared to the amount of the microorganism to be determined, and allowing the first antibody to react with microorganisms in the test sample;

step (ii) adding insolubilized cell walls of a second strain belonging to the species of microorganism to be determined, the second strain having a low affinity to to the first antibody in step (i) in comparison with the first strain, to the reaction mixture of step (i), an allowing the cell walls to react with the remaining free first antibody which has not been bound with the microorganisms to be determined, to form a cell walls-antibody precipitate;

step (iii) separating the precipitated cell walls-antibody complex formed in step (ii);

step (iv) adding a labelled second antibody having affinity for the first antibody to the complex in order to form cell walls-antibody-labelled second antibody complex;

step (v) washing the complex formed in step (iv); and then, step (vi) measuring the activity of labelling substance in the complex.

* * * * *